United States Patent
Langer et al.

(12)

(10) Patent No.: US 6,429,344 B1
(45) Date of Patent: Aug. 6, 2002

(54) PROCESS FOR THE PREPARATION OF D,I-MENTHOL

(75) Inventors: Reinhard Langer, Tönisvorst; Gerd-Michael Petruck, Erkrath, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/439,770

(22) Filed: Nov. 15, 1999

(30) Foreign Application Priority Data

Nov. 20, 1998 (DE) .......................... 198 53 562

(51) Int. Cl.[7] .............................................. C07C 27/00
(52) U.S. Cl. ....................................................... 568/830
(58) Field of Search .......................................... 568/830

(56) References Cited

U.S. PATENT DOCUMENTS

| 2,843,636 A |   | 7/1958 | Booth | 260/631 |
| 2,871,272 A | * | 1/1959 | Bottoms | 568/830 |
| 3,078,316 A | * | 2/1963 | Bottoms | 568/830 |
| 3,946,087 A | * | 3/1976 | Hillion | 568/830 |
| 4,058,571 A |   | 11/1977 | Biedermann | 260/631 |
| 4,058,572 A | * | 11/1977 | Kane | 568/830 |
| 5,300,706 A |   | 4/1994 | Immel et al. | 568/830 |
| 5,750,803 A | * | 5/1998 | Darsow | 568/830 |

FOREIGN PATENT DOCUMENTS

| DE | 197 18 116 | 11/1998 |
| GB | 1415486 | 11/1975 |

OTHER PUBLICATIONS

Solodar, J. Org. Chem., vol. 41, pp. 3461–4364 (1976).*

* cited by examiner

*Primary Examiner*—Michael L. Shippen
(74) *Attorney, Agent, or Firm*—Joseph C. Gil; Noland J. Cheung

(57) ABSTRACT

The invention relates to a process for the preparation of d,l-menthol by catalytic hydrogenation of compounds which have the carbon skeleton of menthane containing at least one double bond and are 3-substituted by oxygen and/or of menthone or isomenthone or mixtures of such compounds using hydrogen at temperatures of 100 to 200° C. and at hydrogen partial pressures between 2 and 50 bar and/or by rearrangement of menthol stereoisomers in the presence of hydrogen at temperatures of 0 to 140° C. and at hydrogen partial pressures between 0.1 and 20 bar in the presence of noble-metal-containing catalysts.

11 Claims, No Drawings

PROCESS FOR THE PREPARATION OF D,I-MENTHOL

FIELD OF THE INVENTION

The invention relates to a process for the preparation of d,l-menthol by catalytic hydrogenation of compounds which have the carbon skeleton of menthane containing at least one C=C double bond and are 3-substituted by oxygen and/or of menthone or isomenthone or mixtures of such compounds using hydrogen at temperatures of 100 to 200° C. and at hydrogen partial pressures between 2 and 50 bar and/or by rearrangement of menthol stereoisomers in the presence of hydrogen at temperatures of 0 to 140° C. and at hydrogen partial pressures between 0.1 and 20 bar in the presence of noble-metal-containing catalysts.

Surprisingly, it has been found that high hydrogen partial pressures markedly decrease the rate of formation of d,l-menthol, so that high temperatures are necessary to achieve high d,l-menthol contents. At low pressures, particularly high d,l-menthol contents can be achieved at low temperatures.

BACKGROUND OF THE INVENTION

Among the naturally occurring cyclic terpene alcohols, l-menthol occupies a special position owing to its cooling and refreshing action. l-Menthol is the main constituent of peppermint oil and is used in the perfume, flavoring and pharmaceutical industry.

Preparation of menthol by catalytic hydrogenation of compounds which have the resolved into carbon skeleton of menthane containing at least one C=C double bond and are their organoleptic properties. l-Menthol has a characteristic peppermint odor and the refreshing action already mentioned; it is therefore the most valuable of the menthol stereoisomers. Attempts are therefore made to carry out hydrogenation in such a way that as much d,l-menthol, from which l-menthol can be obtained by resolution of the racemate, is formed, or to rearrange as effectively as possible menthol stereoisomers, as arise, for example, in the hydrogenation of thymol.

DE 2,314,813 and EP-A-0,563,611 disclose that aromatic or partially hydrogenated cyclic compounds which have the carbon skeleton of menthane containing at least one C=C double bond and are 3-substituted by oxygen can be hydrogenated with hydrogen and/or stereoisomers of menthol can be rearranged in the presence of hydrogen, a cobalt/manganese catalyst or a fixed-bed catalyst which comprises palladium, ruthenium, rhodium or a mixture of these elements as active constituents and alkali metal hydroxides and alkali metal sulphates as promoters on a support doped with a rare earth (RE) metal and with manganese being used.

U.S. Pat. No. 2,843,636 describes the isomerization of stereoisomers of menthol to give d,l-menthol using hydrogen in the presence of a copper chromite catalyst. In this case, about 5% of hydrocarbons which are no longer reusable are produced.

All of these previously described processes for the preparation of menthol by hydrogenation and isomerization starting from compounds having the carbon skeleton of menthane are carried out at high pressures from 200 to 350 bar and high temperatures from 160 to over 220° C. In none of the processes described is more than 59.8% of d,l-menthol formed starting from thymol.

Since industrial apparatuses for carrying out high-pressure hydrogenations are complex and expensive, and a large amount of energy is needed for the compression of hydrogen to the required pressures, on the processing side also, there is considerable potential for improving the production of d,l-menthol by hydrogenation/isomerization starting especially from thymol.

SUMMARY OF THE INVENTION

The object of the invention was therefore to find a selective and industrially simple process for the preparation of d,l-menthol which makes possible d,l-menthol contents of over 60% in the product mixture and avoids, as much as possible, the formation of unwanted by-products.

It has been found that this purpose can be achieved starting from compounds which have the carbon skeleton of methane containing at least one C=C double bond and are 3-substituted by oxygen and/or from menthone or isomenthone or mixtures of such compounds, for example thymol, if hydrogenation is carried out with hydrogen at temperatures of 100 to 200° C. and at hydrogen partial pressures of 2 to 50 bar and then rearrangement is carried out at 0 to 140° C. and a hydrogen partial pressure between 0.1 and 20 bar and for this, noble-metal catalysts containing elements of subgroup VIII are used.

DETAILED DESCRIPTION OF THE INVENTION

The invention is surprising with respect to the fact that just avoiding high pressures causes a marked acceleration of the formation of d,l-menthol; very particularly, at low temperatures. The invention is further surprising in that particularly high d,l-menthol contents can be apparently achieved at the low temperatures. The invention, therefore, relates to a process for the preparation of d,l-menthol by catalytic hydrogenation of compounds which have the carbon skeleton of menthane containing at least one C=C double bond and are 3-substituted by oxygen and/or of menthone or isomenthone or mixtures of such compounds using hydrogen and/or by catalytic rearrangement of menthol stereoisomers in the presence of hydrogen, characterized in that the hydrogenation is carried out with hydrogen at hydrogen partial pressures between 2 and 50 bar, preferably between 4 and 10 bar and at temperatures of 100 to 200° C., preferably 120 to 180° C., and the catalytic rearrangement is carried out at a hydrogen partial pressure between 0.1 and 20 bar, preferably between 1 and 10 bar, and at temperatures of 0 to 140° C., preferably at 40 to 100° C., particularly preferably at 70 to 90° C. and the catalysts used are noble-metal catalysts containing metals of subgroup VIII.

The process of the present invention can be carried out, for example, batchwise or continuously in the bottom phase with suspended catalysts or in reactors for operating stationary catalyst beds. Suitable reactors for the process of the present invention using suspended catalysts are, for example, stirred tanks, bubble columns and loop reactors, as are known from the prior art.

Suitable reactors for the process of the invention using stationary catalyst beds are, for example, thermostated shell and tube reactors in which the catalyst is situated in the tubes or around the tubes for heat dissipation, or adiabatic tube reactors, preferably having zones for cooling the product stream. The reactor for the hydrogenation is preferably operated cooled and for the isomerization is preferably operated adiabatically.

Preferably, the process of the present invention is carried out in reactors having stationary catalyst beds.

The reactors for stationary catalyst beds can be individual low-pressure steel or steel alloy tubes, which are completely or partially packed with shaped catalyst bodies, whereas in the case of higher tube cross-sectional areas, the use of shaped bodies on trays (for example, wire baskets or similar items) can also be useful; however, tube bundles can also be employed within a collective shell, with the individual tubes, in turn, being completely or partially packed with the shaped bodies.

The above-mentioned reactor types are to be understood as examples and are not to be interpreted restrictively.

The process of the present invention can be carried out continuously in two successive reactors, the first, principally serving for the hydrogenation and the second, principally serving for the catalytic rearrangement.

This reactor cascade can be charged with starting material in such a manner that the mixture of the compounds to be hydrogenated is first hydrogenated in the first reactor to give a mixture of the isomeric menthols to which are admixed menthols to be recycled before being fed into the rearrangement reactor, wherein the menthols are produced, for example, in the isolation of l-menthol, but the menthols to be recycled can alternatively be completely or partially run into the hydrogenation reactor together with the mixture to be hydrogenated.

The process of the present invention can likewise be carried out continuously in a reactor in which the conditions are favorable for both the hydrogenation and the isomerization. In a process of the present invention having only one reactor, preferably, pressures between 2 and 10 bar and temperatures between 100 and 120° C. are employed.

If the process is carried out batchwise in one reactor, preferably, first, the reaction conditions which are favorable for the hydrogenation are set and then the reaction conditions favorable for the rearrangement are set.

Preferably, the process of the present invention is carried out continuously.

The technical arrangement of processes of this type is known to those skilled in the art and is not part of the invention.

The process of the invention is a two-stage process which can proceed, if appropriate, simultaneously or successively in one reactor, preferably the catalytic rearrangement is carried out separately in time or space under the low-pressure conditions, which are particularly expedient for it at a hydrogen partial pressure between 0.1 and 20 bar, preferably between 1 and 5 bar and at temperatures of 0 to 140° C., preferably at 40 to 100° C., particularly preferably at 70 to 90° C., with the catalysts used being noble-metal catalysts containing metals of subgroup VIII.

The amount of hydrogen for the hydrogenation step can be between 2 times and 100 times, preferably between 4 times and 50 times, the amount which is required stoichiometrically for the hydrogenation.

For the catalytic rearrangement, the liquid phase must only be in equilibrium with any desired amount of a gas phase having a hydrogen partial pressure between 0.1 and 10 bar, preferably between 1 and 5 bar, i.e. the rearrangement can be carried out, for example, in such a manner that a mixture of the isomeric menthols, as is produced in the hydrogenation, if appropriate, is mixed with menthols which are to be recycled and are produced in the isolation of l-menthol and is correspondingly saturated with hydrogen in order then to be contacted with the catalyst, in which case the presence of a gas phase can be omitted.

For the process of the present invention, catalysts are required which comprise noble metals of subgroup VIII of the Periodic Table of the Elements. Preference is given to catalysts which comprise, as active constituents, in total 0.05 to 10% by weight of ruthenium and if appropriate 1 to 50% by weight, relative to the ruthenium content, of one or more metals of subgroup VIII of the Periodic Table of the Elements on alkalized supports.

Starting compounds for the preparation of the catalysts of the invention are, therefore, compounds of noble metals of subgroup VIII of the Periodic Table of the Elements and when they are present, those of RE (rare earths) and Mn. Those, which may be mentioned, are for example, the halides, nitrates, acetates, organic complexes with acetylacetone or amino acids.

Supports for the catalysts according to the invention are those customary for noble metals, such as activated carbons, $SiO_2$, $TiO_2$, kieselguhr, silica gel, $BaCO_3$, $CaCO_3$, ZnO, MgO, pumice, $ZrO_2$ and obviously, also the oxides or oxide hydrates of Mn and RE themselves, preferably aluminas ($Al_2O_3$) in the various modifications, particularly preferably in the α- or γ-modification. Mn and RE are predominantly used as doping of other supports.

Rare earths (RE) are taken to mean the elements of subgroup III of the Periodic Table (Mendeleev), such as scandium, yttrium, lanthanum and the lanthanides. As RE, either one of the elements or a mixture of a plurality of them can be used. This is especially important therefore because crude mixtures of RE, as are industrially available, and in which only one or two of the RE are initially enriched, can also be used. Preferably one or more of the elements selected from the group consisting of yttrium, lanthanum, cerium, praseodymium, neodymium and dysprosium are used. Particularly preferably cerium is used, if appropriate in a cerium-enriched mixture. For the impingement, the RE and manganese are present on the support in the form of their compounds, preferably in oxidic form.

The catalysts for the process of the present invention comprise basic additives. Basic additives are the oxides, hydroxides or carbonates of the alkali metals or alkaline earth metals, preferably NaOH, KOH and $Ba(OH)_2$. In this case, the basic additives can be applied to the catalyst support prior to or after the metal coating. The alkaline compounds are applied in amounts of 0.1 to 20, preferably 0.2 to 15, particularly preferably 0.3 to 10% by weight, these contents being based on the total weight of the catalyst.

To prepare the catalysts, a procedure can be followed in such a way that the noble metals, in the form of suitable salts, and the alkaline reacting compounds are applied in separate operations onto one of the said supports in the form of powder having particle sizes between 0.001 and 0.1 mm or crushed and screened material having particle sizes between 0.1 and 1 mm or shaped bodies such as rod extrudates, pills, beads or granules having diameters of 1 to 10 mm, and the material is dried after each application. The drying is performed in a known manner, for example, at 30 to 200° C. under reduced to atmospheric pressure (1 to 1000 mbar), for instance in a water-jet vacuum. In the preparation, aqueous solutions are preferably used. However, organic solvents, such as alcohols, lower carboxylic acids, lower nitriles, amides and lactones can also be used or used conjointly, provided that the starting materials are soluble therein.

If a support is first coated with RE and Mn, this can be achieved, for example, by impregnating or spraying the support with solutions of suitable salts of these elements. By heating at temperatures, for instance, between 200 and 450° C., the salts of RE and Mn are converted into oxidic compounds adhering to the support. However, the compounds of RE and Mn can be applied by coprecipitation of RE hydroxide and Mn hydroxide mixtures on the impregnated support with alkali metal, alkaline earth metal or $NH_3$ and if appropriate, subsequent extraction of soluble contents using water. The support, thus pretreated, is dried and then preferably heated for between 1 and 120 h at 200 to 450° C., preferably 250 to 430° C., in which case, the temperature can also be gradually increased within the specified range. The acetates or nitrates of RE and Mn are used, for example.

The supports thus prepared are then impregnated or sprayed with solutions of the noble metals, preferably ruthenium. For this purpose, for example, the chlorides, acetates and nitrates are used. This application of the noble metals can be performed in one step using dissolved mixtures of the salts or successively using the solutions of the individual compounds. After each application, the catalyst should be dried. However, the support impregnated with noble metal can also be treated before the drying with a solution of the abovementioned alkali metal compounds or alkaline earth metal compounds, the noble metal precipitating out as oxide or hydroxide. This can be followed by an extraction of soluble contents and finally again, a drying. However, the catalyst can also be prepared in such a manner that the support coated with RE-Mn is initially impregnated with a solution of the said basic compounds, dried and thereupon, the solutions of the noble-metal salts are applied, the oxides and hydroxides of the noble metals precipitating out. After a washing with water to remove soluble contents and drying, the catalyst can be activated and used for the hydrogenation. A treatment with alkali metal compounds or alkaline earth metal compounds prior to the application of the noble-metal compounds is thus, not absolutely required. However, it is essential that the catalyst is treated with alkali at some time-point of the preparation.

A support prepared in the known manner is available in principle for the use according to the present invention after the final drying phase. However, preferably, before use, it is activated by treatment with hydrogen or hydrogen-nitrogen mixtures containing more than 1% of hydrogen at a temperature of 80 to 400° C., preferably 150 to 350° C.

For bottom-phase processes, for example in stirred tanks, preferably, catalytically active material is used which has a particle size between 0.01 and 0.5 mm, particularly preferably between 0.02 and 0.1 mm.

For the hydrogenation step using stationary catalyst beds, preferably, use is made of catalytically active material which has a particle size between 0.1 and 10 mm, particularly preferably between 1 and 3 mm.

For the rearrangement step using stationary catalyst beds, preferably, use is made of catalytically active material which has a particle size between 0.1 and 2 mm, particularly preferably between 0.3 and 1 mm.

The starting compounds used for the process of the present invention are known (Ullmanns Encyclopädie der Technischen Chemie [Ullmann's Encylopaedia of Industrial Chemistry], 3rd edition, volume 17, Munich 1966, pp. 24/25; U.S. Pat. No. 2,843,636). Those which may be mentioned by way of example, are menthone, isomenthone, isomenthol, d-menthol, d- and l-neomenthol, d- and l-isomenthol, d,l-neomenthol. d,l-isomenthol, d,l-neoisomenthol, d,l-neoisomenthone, and thymol; preferably thymol. These compounds can be used both individually and in any mixtures with one another.

The catalyst space velocity for the hydrogenation step is 0.05 to 5 g of starting material per ml of catalyst per hour, preferably 0.1 to 2.5 g/ml·h, particularly preferably 0.2 to 1.2 g/ml·h and, for the catalytic rearrangement, is 0.01 to 1 g/ml·h, preferably 0.05 to 0.5 g/ml h, particularly preferably 0.1 to 0.3 g/ml h.

The hydrogenations, racemizations and isomerizations taking place in the process of the present invention surprisingly lead to the scarce formation of unusable byproducts, such as unwanted hydrocarbons.

The resultant reaction mixture has a very high content of d,l-menthol, which can be worked up to give the desired product by rectification/distillation. Using the process of the present invention, not only are excellent results obtained in the hydrogenation of thymol, but excellent yields are also obtained in the conversion of the other. above-mentioned starting compounds.

After separating off the wanted d,l-menthol by distillation, the distillation first runnings together with the distillation bottom phase with addition of fresh starting material, for example with addition of 10 to 80% by weight of thymol, based on the residual reaction products present in the distillation first runnings and in the distillation bottom phase, can be recycled back into the reaction. The amount of starting material equivalent to the d,l-menthol removed by distillation is replaced. The hydrogen not consumed in the process of the invention can be recycled.

The d,l-menthol produced, after removal of the distillation first runnings and the distillation bottom phase, is obtained in a purity of $\geq 99.9\%$ by weight, and can, therefore, be used for all further processes without further purification. The colourless and glass-clear product obtained after the distillation has a melting point of 41° C. and can be crystallized in crystallization apparatuses of customary type.

The process of the invention can be carried out in the presence of solvents, but a solvent-free procedure is preferred.

In the examples below, the $m^3$ (S.T.P.) denotes cubic meters after conversion to standard conditions (1 bar, 25° C.).

The invention is further illustrated but is not intended to be limited by the following examples in which all parts and percentages are by weight unless otherwise specified.

EXAMPLES

Example 1 (Preparation of a Catalyst Support)

5.0 l (4.01 kg) of a commercial $\gamma$-$Al_2O_3$ having a BET surface area of 310 $m^2/g$ as crushed material of 1 to 2 mm in diameter (SPH 501 from Rhone-Poulenc) were stirred with 1.89 l of an aqueous solution of 248 g of $Ce(NO_3)_3 \cdot 6 H_2O$ and 365.5 g of $Mn(NO_3)_2 \cdot 4 H_2O$ until the solution was completely absorbed and then dried under reduced pressure at 100° C. Then, 1.75 l of an aqueous solution of 204 g of NaOH were applied in the same manner, allowed to stand for 24 h and then washed with water until nitrate-free, dried under reduced pressure at 100° C. and finally calcined for 4 h at 400° C.

Example 2 (Preparation of an Ru Catalyst)

1000 g of the support as described in Example 1 were impregnated with 100 g of $RuCl_3$ (20% Ru) in 60 g of distilled water, dried (3 h, 100° C., reduced pressure) and reduced with $H_2$ at 250° C. in 3 h. The catalyst was washed chloride-free with distilled water and dried. Finally, there followed an impregnation with 50 g of NaOH in 150 g of $H_2O$ and a 3 hour vacuum drying at 100° C.

Example 3 (Preparation of a Fine-grained Ru Catalyst)

The preparation was repeated as described in Examples 1 and 2 with the exception that crushed and screened support having a particle size between 0.5 and 1.0 mm was used.

Example 4

A tube reactor consisting of 5 oil-thermostated reactor tubes was packed with the catalysts from Examples 2 and 3. The reactor tubes had an internal diameter of 2 cm and a bed length of 80 cm, so that each tube holds approximately 250 ml of catalyst bed.

The upper two reactor tubes were packed with a total of 500 ml of catalyst from Example 2 and the lower three reactor tubes with 750 ml of catalyst from Example 3. 200 l (S.T.P.) of hydrogen per hour flowed through the catalyst bed for 20 h at 4 bar at 150° C.

The upper two reactor tubes were then thermostated to approximately 1 80° C. and the lower three tubes to approximately 80 to 90° C.

At a hydrogen pressure of 3 bar, thymol was trickled from top to bottom over the bed at a space velocity of 0.13 g per ml of catalyst and hour.

The hydrogen flow through the reactor was a constant 220 l (S.T.P.)/h.

The thymol content in the liquid phase decreases to markedly below 1% even after the uppermost reactor tube. The d,l-menthol content increases from reactor tube to reactor tube. After the first reactor tube, approximately 48–52% is found in the liquid phase, after the second tube approximately 54%, after the third tube approximately 60%, after the fourth tube approximately 63% and at the reactor outlet approximately 64% of d,l-menthol.

The reaction product consists of approximately 0.24% of trans-menthane, 0.2% of cis-menthane, 0.02% of menthone, 0.015% of isomenthone, 20.8% of neomenthol, 0.8% of neoisomenthol, 12.1% of isomenthol and 64.4% of menthol. The reaction mixture contained approximately 1.4% of other intermediates.

The catalyst operated under the specified conditions for 500 h without significant deactivation, whereupon the experiment was terminated.

Example 5

An equimolar mixture of neomenthol, isomenthol and neoisomenthol which was saturated with hydrogen at 1 atm was pumped at 70° C. via a 2 m-long catalyst bed which was prepared as described in Example 3. The diameter of the thermostated bed was 2 cm.

In the reactor, only the catalyst bed and the liquid phase were situated, but no gas phase.

The space velocity of the catalyst bed was approximately 0.1 kg/l×h.

The reaction product contained approximately 65% of d,l-menthol.

The composition was 20.8% of neomenthol, 0.8% of neoisomenthol, 65.3% of menthol, 12.1% of isomenthol and 0.9% of other intermediates.

The experiment ran approximately 500 hours without any indication of the start of deactivation.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of d,l-menthol by catalytic hydrogenation of a starter selected from the group consisting of thymol, isomenthol, d-menthol, d- and l-neomenthol, d- and l-isomenthol, d,l-neomenthol, d,l-isomenthol, d,l-neoisomenthol, and mixtures thereof, using hydrogen and by catalytic rearrangement of menthol stereoisomers in the presence of hydrogen, wherein hydrogenation is carried out with hydrogen at hydrogen partial pressures between 2 and 50 bar and at temperatures of 100 to 200° C. and the catalytic rearrangement is carried out at a hydrogen partial pressure between 0.1 and 20 bar and at temperatures of 0 to 140° C. and the catalysts used are noble-metal catalysts containing metals of subgroup VIII, wherein the d,l-menthol content of the catalytic rearrangement reaction mixture is over 60%.

2. A process according to claim 1, wherein the process is carried out continuously.

3. A process according to claim 1, wherein said catalysts comprise, as active constituents, in total 0.05 to 10% by weight of ruthenium.

4. A process according to claim 3, wherein, in addition to the ruthenium, 1 to 50% by weight, relative to the ruthenium content, of one or more metals of subgroup VIII of the Periodic Table of the Elements are present on alkalized supports.

5. A process according to claim 4, wherein the alkalized supports are doped with compounds of the rare earth metals and of manganese, the total amount of rare earth metals and manganese, calculated as metals and based on the total weight of the catalyst, being 0.05 to 8% by weight and the weight ratio of rare earth metals and manganese to one another being 5:1 to 1:5.

6. A process according to claim 5, wherein the alkalization of the catalyst supports leads to a content of oxides, hydroxides or carbonates of alkali(ne earth) metals or a mixture of a plurality of them in an amount of 0.1 to 20% by weight.

7. A process according to claim 5, wherein the rare earth metal is selected from the group consisting of yttrium, lanthanum, cerium, praseodymium, neodymium and dysprosium.

8. A process according to claim 1, wherein said starter is thymol.

9. A process according to claim 1, wherein the catalyst space velocity in the hydrogenation is 0.05 to 5 g of starting material per ml of catalyst per hour (g/ml·h) and in the catalytic rearrangement is 0.01 to 1 g/ml·h.

10. A process according to claim 1, wherein the d,l-menthol is taken off from the reaction product of hydrogenation and rearrangement by distillation and the residual reaction products are recycled into the reaction with addition of 10 to 80% by weight of thymol, based on the residual reaction products.

11. A process according to claim 1, wherein the catalysts used are prepared by impregnating the supports with solutions of halogen-containing noble-metal salts.

* * * * *